United States Patent [19]
Latva et al.

[11] Patent Number: 5,998,146
[45] Date of Patent: Dec. 7, 1999

[54] HOMOGENEOUS LUMINESCENCE ASSAY METHOD BASED ON ENERGY TRANSFER

[75] Inventors: Martti Latva, Turku; Ilkka Hemmilä, Kaarina; Kaj Blomberg, Turku; Pertti Hurskainen, Piispanristi, all of Finland

[73] Assignee: Wallac Oy, Turku, Finland

[21] Appl. No.: 09/116,763

[22] Filed: Jul. 17, 1998

[51] Int. Cl.⁶ .................................................. C12Q 1/68
[52] U.S. Cl. ........................ 435/6; 436/501; 935/77; 935/78
[58] Field of Search ........................ 435/6; 436/501; 935/77, 78

[56] References Cited

U.S. PATENT DOCUMENTS

| | | | |
|---|---|---|---|
| 4,822,733 | 4/1989 | Morrison | 435/6 |
| 5,278,043 | 1/1994 | Bannwarth et al. | 536/23.1 |
| 5,279,943 | 1/1994 | Mathis et al. | 435/7.32 |
| 5,512,493 | 4/1996 | Mathis et al. | 436/537 |
| 5,622,821 | 4/1997 | Selvin et al. | 435/6 |
| 5,631,169 | 5/1997 | Lakowicz et al. | 436/537 |
| 5,639,615 | 6/1997 | Selvin et al. | 435/6 |
| 5,656,433 | 8/1997 | Selvin et al. | 435/6 |

FOREIGN PATENT DOCUMENTS

| | | |
|---|---|---|
| 2223096 | 3/1990 | United Kingdom . |
| WO 87/07955 | 12/1987 | WIPO . |
| WO 98/15830 | 4/1998 | WIPO . |

OTHER PUBLICATIONS

Selvin et al., J. Am. Chem. Soc., vol. 116, pp. 6029–6030, 1994.

Heyduk et al., Analytical Biochemistry, vol. 248, pp. 216–227, 1997.

Li et al., "Luminescent Polyaminocarboxylate Chelate of Terbium . . . ," 117 *J. Am. Chem. Soc.* 8132–38 (1995).

Li et al., "Amine–Reactive Forms of a Luminescent . . . ," 8 *Bioconjugate Chem.* 127–132 (1997).

Mathis, "Rare Earth Cryptates and Homogeneous . . . ," 39 *Clin. Chem.* 9, 1953–59 (1993).

Matko et al., "Luminescence Quenching by Long Range . . . ," 19 *Cytometry* 191–200 (1995).

Morrison, "Detection of Energy Transfer . . . ," *Nonisotopic Probing, Blotting, and Sequencing* 429–471 (Academic Press Inc., 1995).

Morrison, "Time–Resolved Detection of Energy Transfer . . . ," 174 *Anal. Biochem.* 101–120 (1988).

Selvin, "Fluorescence Resonance Energy . . . ," 246 Methods in *Enzymol* 300–335 (1995).

Stryer et al., "Diffusion–Enhanced Fluorescence . . . ," 11 *Ann. Rev. Biophys. Bioeng.* 203–222 (1982).

Thomas et al., "Transverse Location of the Retinal . . . ," 154 *J. Mol. Biol.* 145–157 (1982).

Wu et al., "Resonance and Energy Transfer . . . ," 218 *Anal. Biochem.* 1–13 (1994).

*Primary Examiner*—Ardin H. Marschel
*Attorney, Agent, or Firm*—Lydon & Brown, LLP

[57] ABSTRACT

The invention is a luminescence energy transfer based bioaffinity assay comprising a first group labeled with an energy donating compound (donor) and a second group labeled with an energy accepting compound (acceptor), wherein the donor is a luminescent lanthanide chelate having a long excited state lifetime and the acceptor is either a luminescent compound having a short excited state lifetime or a nonluminescent compound. The increase or decrease, respectively, in the energy transfer from the donor to the acceptor resulting from shortening or lengthening, respectively, of the distance between the said groups, is measured. Characteristic for the invention is that the lanthanide energy emission and the acceptor energy absorption do not essentially or not at all overlap each other.

13 Claims, 4 Drawing Sheets

Fig.4

HOMOGENEOUS LUMINESCENCE ASSAY METHOD BASED ON ENERGY TRANSFER

FIELD OF THE INVENTION

The present invention relates to an improvement in energy transfer based bioanalytical assay technology which use lanthanide chelates as labels. The improvements relate to two variations of the technology applied in different types of assays; assays where dissociation is measured and assays where association is measured. In the first type of assay the preferred assay configuration is fluorescence quenching assay and the release, or dissociation of labeled compound e.g. upon hydrolysis, is followed by the fluorescence increase. In the second type of assay the preferred configuration is composed of measuring of increase in energy transfer upon complex formation once the distances between donor and acceptor labels are shortened. The specific improvement of the technologies relates to how the quenching and/or enhancement of energy transfer can be exploited when using lanthanide chelates as donors. According to the invention the nonoverlapping principle allows one to extend the assortment of acceptor molecules, wavelength range, improved sensitivity and applications of multilabel systems.

BACKGROUND OF THE INVENTION

The publications and other materials are used herein to illuminate the background of the invention, and in particular, cases to provide additional details respecting the practice, are incorporated by reference.

A great variety of assays based on bioaffinity or enzymatically catalyzed reactions have been developed in order to analyze biologically important compounds from various biological samples (such as serum, blood, plasma, saliva, urine, feces, seminal plasma, sweat, liquor, amniotic fluid, tissue homogenate, ascites, etc.), samples in environmental studies (natural, raw and waste water, soil samples) industrial processes (process solutions, products and side products) and compound libraries (screening libraries which may comprise organic compounds, inorganic compounds, natural products, extracts of biological sources, biological proteins, peptides, or nucleotides, and so on). These association assays rely on specific bioaffinity recognition reactions, in which natural biological binding components form the specific binding assay (using biological binding components such as antibodies, natural hormone binding proteins, lectins, enzymes, receptors, DNA, RNA or peptide nucleic acids (PNA)) or artificially produced binding compounds like genetically or chemically engineered antibodies, molded plastic imprint (molecular imprinting) and so on. Such assays generally rely on a label to quantitate the formed complexes after recognition and binding reactions and suitable separation. To achieve efficient separation of bound reagents from unbound components separations such as precipitation and centrifugation, filtration, affinity collection (to e.g. plastic surfaces of tubes, slides or microbeads), solvent extraction, gel filtration or other chromatographic systems are used. The quantitation of the label in free or bound fraction enables the calculation of the analyte in the sample directly or indirectly, generally through use of a set of standards to which unknown samples are compared.

Dissociation assays are assays where, for example specific enzymes catalyze a biological reaction such as hydrolyzing a substrate, transferring a functional group, adding or cleaving a substituent and so on. On the contrary to binding assays some of those assays follow the hydrolysis of a labeled product, e.g. enzyme substrate. According to assay design, a wide variety of different labeling technologies are applied. These assays can utilize a simple labeled substrate, which facilitates the measurement of either substrate or end product, or it may be defined in a way to give direct information of hydrolysis (e.g. internal quenching or energy transfer).

The separation and washing needed in most of these assays make them labor intensive, slow and difficult to automate. Furthermore end point measurement does not allow gathering of kinetic information (e.g. association/dissociation rates). In cases of low affinity bindings, the affinity may be so low that no physical separation can be applied without destroying the binding (e.g. low affinity receptors). Particularly in areas, like screenings (e.g. high throughput screening) there is a constant demand for simpler assays, simplified protocols, which would make automation easier and increase the throughput.

This can be accomplished with homogeneous or nonseparation assays. Homogeneous biomedical assays are defined as assays taking place in one homogeneous phase. It means that no separate phases (such as solid phase catching reagents), and no separation is used prior to measurement. This requires a signal production system that responds to the binding in a way making its direct monitoring possible. Systems known to prior art are e.g. fluorescence polarization assays applied for small molecular compounds, enzyme-monitored immunoassays (Syva Co.), various fluorescence quenching or enhancing assays (for an review see e.g. Hemmilä, Applications of Fluorescence in Immunoassays, Wiley, N.Y., 1991). Another category of simplified assay technologies is the nonseparation assays, which, similarly to homogenous assays, avoid separation and washing steps. A good example of such a technology is the scintillation proximity principle marketed by Amersham, which is based on short distance penetration of radiation particles in assay medium and a solid scintillator coated with catching reagents (Udenfriend et al, (1985) Proc Natl Acad Sci, 82, 8672 and Anal Biochem, (1987) 161, 494).

Regardless of a great number of homogeneous assay designs published to day, there are no assays, where the versatility and sensitivity would match those of a good separation assay. The reason to that is manifold relating to e.g. the different way a homogeneous, versus heterogeneous, assay has to be optimized, the control of low affinity nonspecific bindings, and the limitations of applicability of most of the existing homogenous assay techniques. In addition, the conventional homogeneous fluorometric assays are very vulnerable to background interferences derived from various components in the samples. Fluorescence polarizations assays are interfered by low affinity nonspecific bindings (e.g. probe binding to albumin) and autofluorescence of samples.

Energy transfer is a widely used technology to measure and monitor biological reactions. Fluorescence resonance energy transfer (FRET) has been applied e.g. as a spectroscopic ruler in structural studies to measure distances within a macromolecule (Stryer and Haugland (1967) Proc Natl Acad Sci. USA, 58; 719). In addition to resonance energy, transfer, there are other energy transfer reactions, like simple radiative energy transfer (where acceptor absorbs the light emitted by donor), collisional energy transfer, exchange mechanism (Dexter (1953) J Chem Physics, 21, 836), exciton migration (in crystals) and long range electron transfer (Matko et al. 1995, Cytometry 19, 191). In addition, donor emission can be quenched by numerous ways with a number of unrelated compounds having a deactivating effect on some of the donor's energy levels.

Resonance Energy Transfer

The Förstr type of nonradiative dipole—dipole energy transfer (Förster (1948) Ann Physik, 6, 55, Selvin P, Methods in Enzymology 246, 300 1995) takes place between two molecules in conditions where their energies (emission of donor with absorption of acceptor) overlap and they are at a distance less than 20 nm. The energy transfer requires a proper orientation of the oscillations of the molecules. The energy transfer efficiency ($\Phi_{ET}$) is given in the equation:

$$\Phi_{ET}=1/[1+(r/R_0)^6] \quad [\text{Eq.1}]$$

where r is the distance between the donor and acceptor molecules and $R_0$ is a distance parameter characteristic of the donor-acceptor pair and the medium between them.

The Förster radius, $R_0$ is defined by equation 2 [Eq. 2]

$$R_0=(8,79\times10^{-5}J\times\Phi_D\times n^{-4}\kappa^{-2})^{1/6} \quad [\text{Eq.2}]$$

where J is the spectral overlap of donor emission and acceptor absorption, $\Phi_D$ is the quantum yield of free donor, n is the refractive index of medium, and $\kappa^2$ is the geometric rate constant.

It is noteworthy that in all equations published so far, energy transfer is a direct function of the spectral overlapping factor J.

FRET has found extensive applications, not only in basic research, but also in various bioanalytical technologies. Ullman was the first to describe application of Förster-type nonradiative energy transfer in bioanalytical assays based on an antibody recognition reaction (Ullman, Schwarzberg and Rubenstein (1967) J Biol Chem, 251; 4172) marketed as FETIA (fluorescence energy transfer immunoassay) by Syva Co. (U.S. Pat. No. 3,996,345). Development of suitable energy donor-acceptor pairs are well described in their various reviews (Ullman and Khanna (1981 ) Methods Enzymol, 74; 28; Khanna and Ullman (1980) Anal Biochem, 108, 156). FETIA primarily applies xantlene dyes and derivatives of fluorescein as donors and rhodamines as acceptors. A great number of alternative probe pairs have since been developed and applied in immunoassays (for a review see Hemmilä 1991, chapter 8.3.4) including practically nonfluorescent derivatives of fluorescein long life-time delayed fluorescence emittive eosin (Thakrar and Miller (1982) Anal Proc, 19, 329), long lifetime fluorescent pyrene (Morrison (1988) Anal Biochem, 174, 101) and nonemittive charcoal. FRET has since got wide applications in basic research and in DNA hybridizations (see e.g. Morrison et al ( 1989) Anal Biochem, 183, 231; Parkhurst et al (1995) Biochemistry, 34, 285) and other assays were association, dissociation or distances are to be measured.

In addition to association assays, energy transfer is an essential technology in a variety of enzymatic assays (assays measuring dissociations). Examples can be found e.g. in detection of proteases and peptidases using internally quenched substrates (WO 94-28166, WO 91-16336 and U.S. Pat. No. 4,822,746) and use of double-labeled peptide substrate in reporter gene assays (WO 97-28261 and WO 96-30540). FRET has got numerous applications also in molecular biology, for automated detection of PCR products, sequencing (U.S. Pat. No. 5,707,804) etc.

Time-resolution in FRET

Time-resolved (TR) fluorometry (time resolution in time-domain at micro- or millisecond range) is a perfect measuring regime for homogeneous assays, because it can totally discriminate the background fluorescence derived from organic compounds. When long enough delay times (time between pulsed excitation and starting of emission recording) can be used, all background interferences can be eliminated (for a review see. e.g. Hemmilä(1991); Gudgin Dickinson et al, (1995) J Photochem Photobiol 27, 3). In addition to separation based assays, also a number of homogeneous time resolved fluorometric assays have been described and patented (Mathis (1995) Clin Chem, 41, 1391; Selvin et al. (1994) Proc Natl Acad Sci, USA, 91, 10024) with their limitations and drawbacks.

The use of temporal discrimination (time-resolution) to avoid the effect of direct excitation of acceptor molecules was first described by Morrison (Morrison (1988) Anal Biochem, 174, 101). He used organic donor-acceptor pairs of different decay times; pyrene as the long excited state donor, pulsed laser for excitation and phycoerythrin as the short decay-time acceptor (U.S. Pat. No. 4,822,733). In addition to immunoassays, the time-resolved energy transfer principle is applied for homogeneous solution hybridization using fluorescein (Morrison et al (1989) III rd International Symposium on Quantitative Luminescence Spectrometry in Biomedical Sciences, Ghent Belgium) as acceptor. The long excited state provides the advantage, that specific energy transfer can be followed using a delay time, during which the emission of a directly excited acceptor has decayed off. The combination of different decay times exploited in time-resolved fluorometry will provide a clear advantage over FRET technologies employing conventional short decay probes.

Lanthanides and their chelates are good candidates for time-resolved FRET experiments. Firstly, they have exceptionally long excited state lifetime (Weissman (1942) Chem Phys, 10, 214; Whan and Crosby (1962) Mol Spectrosc, 8, 315). The energy transfer takes place only between transitions that are electric dipole. The major transition in the highly fluorescent Eu chelates, (transition $^5D_0 - {^7F_2}$, FIG. 1) at 612–620 nm is electric dipole forced (Bünzli (1989) Lanthanide Probes in Life, Chemical and Earth Sciences. Theory and Practice, Bünzli and Choppin (ed.) Elsevier Science, Publisher, Amsterdam) and can donate energy. The transition $^5D_0 - {^7F_1}$ producing emission at 590–595 nm is, however, magnetic dipole and can not transfer energy (Dexter, J Chem Phys 21: 836, 1953). In addition, lanthanide emission has isotropic moment, and hence the orientation factor becomes less ambiguous (Ando et al (1992) Biochim Biophys Acta, 1102, 186).

Fluorescent lanthanide chelates have been used as energy donors already since 1978 by Stryer, Thomas and Meares. For example a Tb dipicolinate chelate reported to have the critical distance ($R_0$) of 6.57 nm for rhodamine, 4.46 nm for cosin and 4.46 am for NBD (Thomas et al (1978) Proc Natl Acad Sci, 75: 5746). Typically in an efficient energy transfer, the overall decay shortens from 2.22 ms to 0.12 ms. Meares et al (1981, 1992) measured enzyme bound rifamycin using Tb-phenyl-EDTA as energy donor (Biochemistry 20; 610; Biochemistry 22; 6247). In addition to fluorescent compounds, also nonluminescent acceptors have been reported, such as Co (III) and Co (II) (Cronce and Horrocks (1992) Biochemistry 31, 7963). Eu and Tb chelates have also been tested as energy acceptors, Eu for coumarin derivative and Tb for salicylate derivative (Clark et al (1993) Anal Biochem 210, 1). The great number of available nonluminescent energy acceptors (quenchers) is an additional advantage for lanthanide chelates. They can i, quenched by metallic ions, nitrite (Tanaka et al (1993) J Photochem Photobiol A: Chem, 74, 15), other paramagnetic metallic ions and their chelates, free radicals (Matko et al (1992) Biochemistry 31, 703) and so on.

The complex compounds (chelates) developed relate to various types of multidentate complexes, i.e. chelates. According to various researches they have got different names, but all are based on organometallic complexes derived from a chelated lanthanide ion and a multidentate ligand. The names include supramolecular compounds, complexes, chelates, complexones, cryptates, crown-ether complexes, calixarenes, mixed-ligand complexes and so on.

There are a great number of stable fluorescent chelates, described in patents and articles, which could be used in time-resolved FRET assays, for example those mentioned in the following U.S. Pat. Nos.: 4,761,481; 5,032,677; 5,055,578; 5,106,957; 5,116,989; 4,761,481; 4,801,722; 4,794,191; 4,637,988; 4,670,572; 4.837,169 and 4,859,777. The preferred chelate is composed of a nona-dentate chelating ligand, such as terpyridine (EP-A 403593; U.S. Pat. No. 5,324,825; U.S. Pat. No. 5,202.423. U.S. Pat. No. 5,316,909) or a terpyridine analogue with one or two five-membered rings (e.g. pyrazole, thiazole, mazine) (EP 077061041 and WO 93/11433). Very well suited chelates are also mentioned in the following articles: Takalo et al (1994) Bioconjugate Chem, 5, 278; Mukkala et al (1993) Helv Chim Acta, 76, 1361: Remuinnan et al (1993) J Chem Soc Perkin Trans, 2, 1099; Mukkala et al (1996) Helv Chim Acta, 79, 295; Takalo et al (1996) Helv Chim Acta, 79.

Long life-time emitting fluorochromes, and lanthanide chelates have been used in a number of energy transfer based patents. Wieder and Hale described a homogeneous time-resolved immunoassay based on various techniques, including resonance energy transfer and heavy metal quenching (EP-A 272320 and WO 87/07955), Stavrianopoulos (EP-A 242527, 1987) filed an assay based on the use of a complement factor Clq and FRET. Hoffman La Roche has patented a specific application using lumazine-type of chromophore as donor and a ruthenium chelate as acceptor for interactions between nucleic acids (EP 439036) and Cis Bio International applied for an assay based on Eu or Tb cryptates as donors for phycobiliproteins (WO 92/01225). Selvin et al has patented a TR-FRET assay based on DTPA-derived lanthanide chelates (U.S. Pat. No. 5,622,821, U.S. Pat. No. 5,656,433). Mathis and al. (U.S. Pat. No. 5,279,943) also filed a patent were quenching, similar to heavy metals, is achieved by the nonoverlapping principle using heavy atoms attached to a target compound, which is able to modulate the chelate fluorescence by inter-system transition (undefined mechanism).

Figure 2:
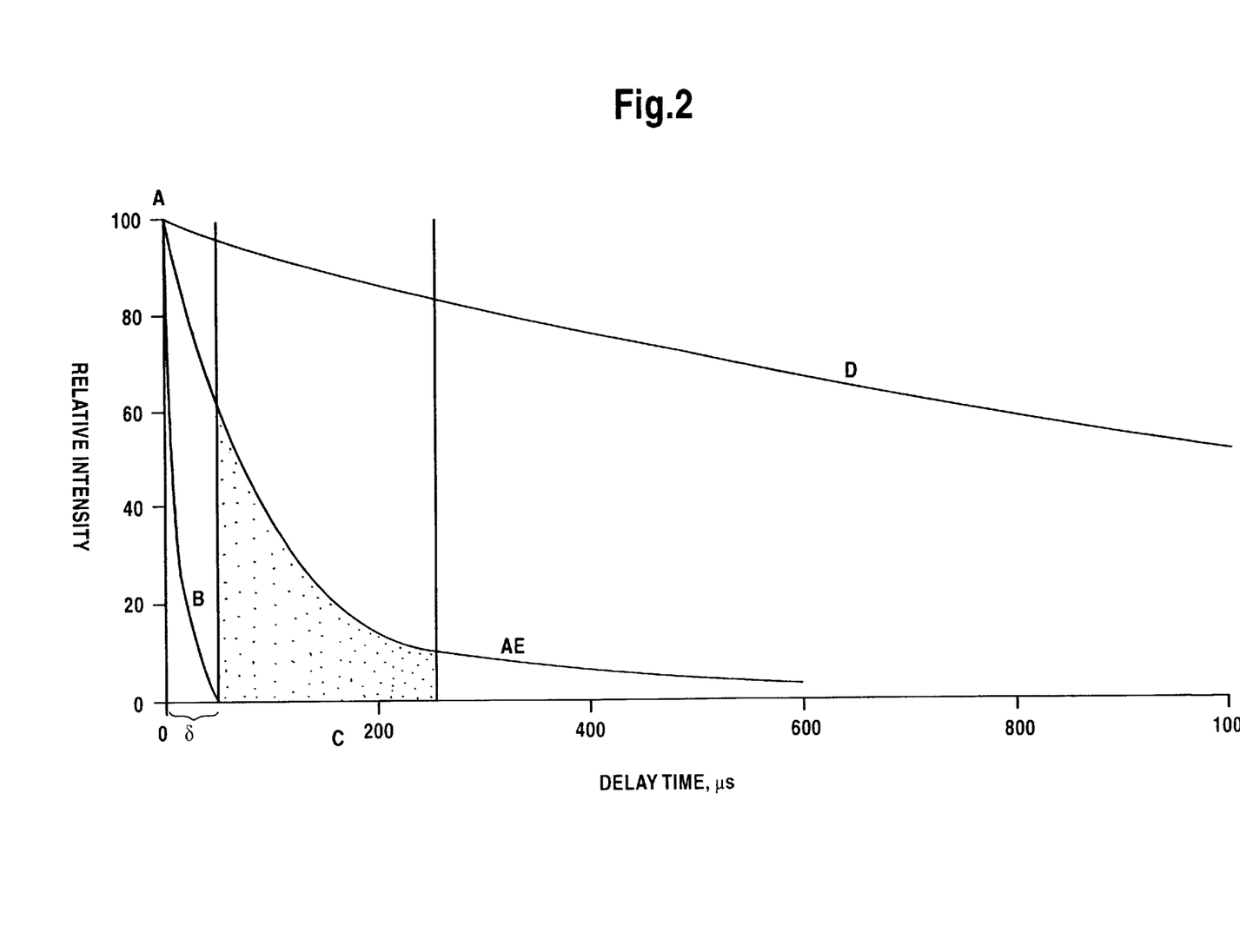
FIG. 2 shows the principle of TR-FRET. In the complex, when donor and acceptor labels are in proximity, the donor energy (D) excited by a short light pulse (A) is transferred by resonance energy transfer to acceptor. The energy transfer excited acceptor emission (AE) can be distinguished from the acceptor emission (B) excited directly by the light pulse (A) by applying a delay time ($\delta$) during which the counts from the photomultiplier tube are not recorded.
Figure 3:
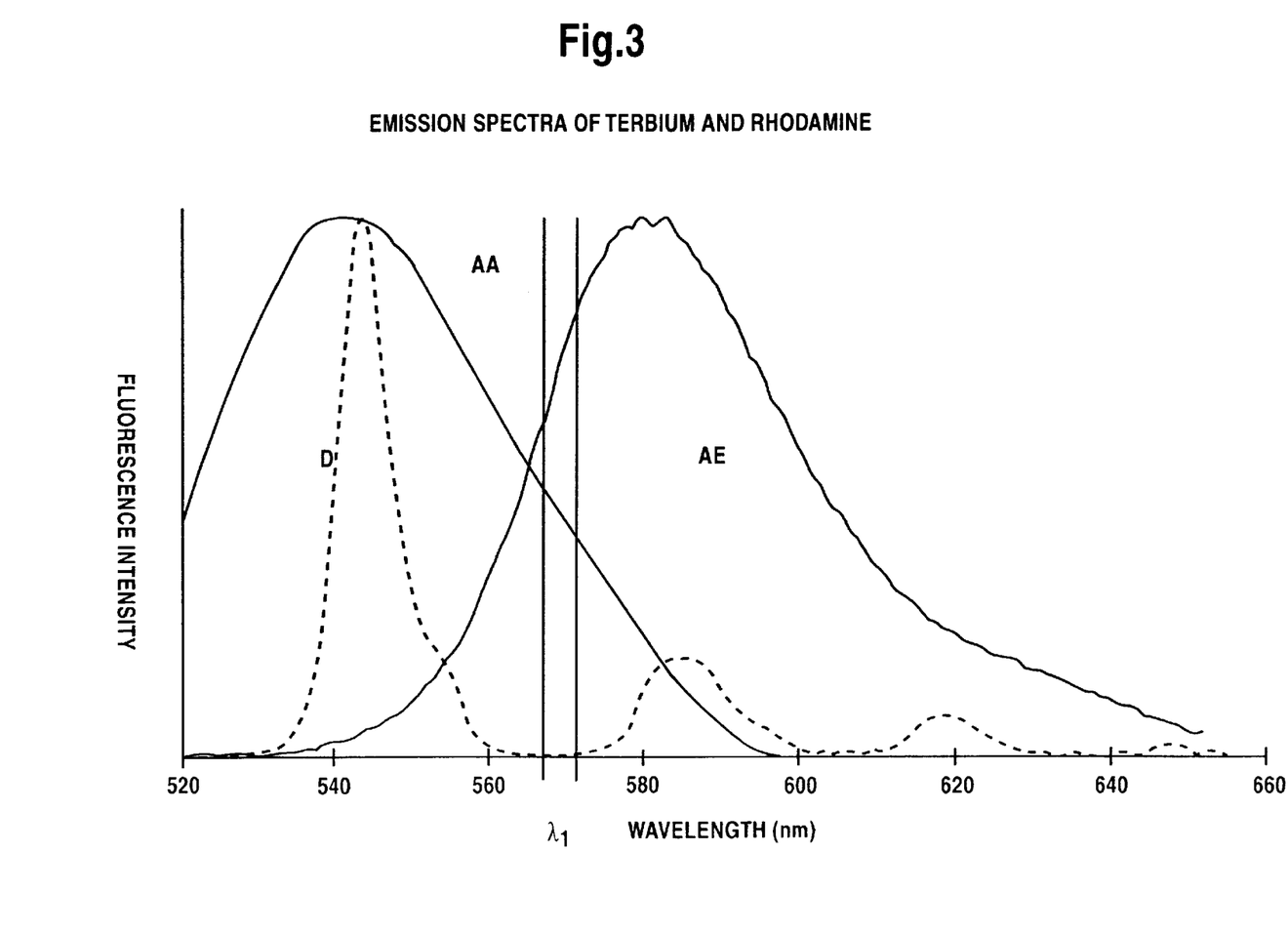
FIG. 3 shows the emission profiles of a traditionally applied donor-acceptor pair (Tb with rhodamine). The rhodamine absorption (AA) overlaps well with the major emission of Tb (D) at 545 nm. Rhodamine emission (AE) at a longer wavelength is recorded using a narrow filter ($\lambda_1$) at a position where Tb gives minimal background.

The principle of a time-resolved homogeneous assay based on a specific energy transfer between a long lifetime donor and a short lifetime emitting acceptor molecule is summarized in FIG. 2. In a homogenous assay based on energy transfer the long-lived donor is excited with a light pulse (A). The luminescence emission (AE) of the energy transfer excited acceptor is measured within the counting window (C) after a suitable delay ($\delta$), to avoid interference derived from directly excited acceptor (B). The long-lived emission from the donor (D) is avoided by measuring the emission (AM) of the energy transfer excited acceptor at a wavelength ($\lambda_1$) where the donor emission is absent or negligible (FIG. 3). Hence, in homogenous bioaffinity assays (receptor-ligand binding, hybridization reaction, immunobinding, enzyme substrate binding etc.) the association or dissociation of donor-acceptor pairs can be followed by measuring the increase or decrease, respectively, in the signal from the energy transfer excited acceptor.

Known energy transfer assays are all based on the principle of spectral overlapping, i.e. the acceptors absorbance (AA) overlaps the donor emission (D) as shown in FIG. 3. Surprisingly the inventors have now found that such spectral overlapping is not a prerequisite for energy transfer.

SUMMARY OF THE INVENTION

The present invention relates to the field of luminescence energy transfer assay comprising a first group labeled with an energy donor and a second group labeled with an energy acceptor, wherein the acceptor is either a short excited state lifetime luminescent label or a nonluminescent label. The increase or decrease, respectively, in energy transfer from the donor label to the acceptor label resulting from shortening or lengthening, respectively, of the distance between said labels, is measured.

The invention is a luminescence energy transfer based bioaffinity assay comprising a first group labeled with an energy donating compound (donor) and a second group labeled with an energy accepting compound (acceptor), wherein the donor is a luminescent lanthanide chelate having a long excited state lifetime and the acceptor is either a luminescent compound having a short excited state lifetime or a nonluminescent compound, and the increase or decrease, respectively, in the energy transfer from the donor to acceptor resulting from shortening or lengthening, respectively, of the distance between the said groups, is measured characterized in that the lanthanide energy emission and the acceptor energy absorption do not essentially or not at all overlap each other.

DETAILED DESCRIPTION OF THE PREFERRED EMBODIMENTS

The present invention relates to improvements of energy transfer based homogeneous assays which use lanthanide based compounds as labels. The specific improvement relates to a wide utilization of all the excited state manifolds of an excited lanthanide ion as energy donating states. The fact discovered in the invention is that energy transfer, used either in assays where dissociation is to be followed, or association based assays were complex formation is followed, i.e. label pair distance shortening is to be followed, is not a direct function of visible spectral overlapping, and hence is not strictly under the generally accepted rules of Förster-type resonance energy transfer, but the energy transfer is more widely a function of energetic overlapping. In energy terms this probably means that the likelihood for energy transfer in a proximity is different as compared to a separate emittive transition of a chelate label in absence of a quencher or acceptor molecule.

Figure 4:
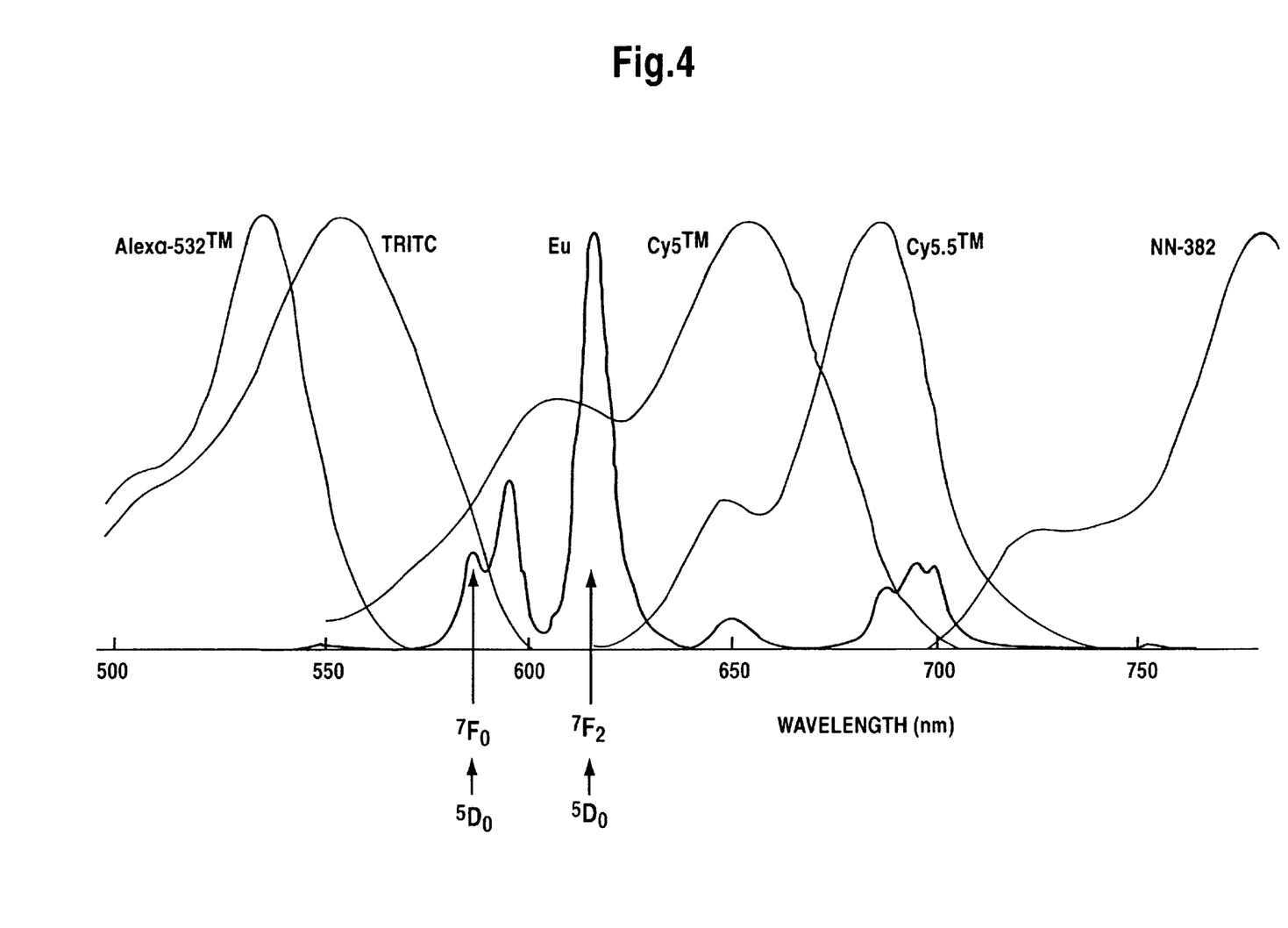
FIG. 4 shows absorption spectra of suitable energy acceptors for Eu. Eu emission (heavy line) is compared to the absorption spectra of tetramethyl rhodamine (TRITC), Alexa 531 (Molecular Probes), Cy5 and Cy5.5 (Pharmacia-Amersham) and NN-382 (Li-Cor). Arrows indicate the positions of the Eu transition of maximal energy (0—0 transition) and the major emission.

On the contrary to prior art and the way the acceptor has been chosen in all prior art methods, the acceptor used in the present invention is a resonance energy transfer acceptor, a light absorbing aromatic compound wherein the donor energy emission and the acceptor energy absorption do not essentially or not at all overlap each other. Spectral overlapping can be assessed from spectral data. The absorbance of all acceptors in FIG. 4 have none or minor overlapping with the emission of the donor except for Cy5. Cy5 has major overlapping with Eu when presented on same arbitrary scale: more than 50% of Eu emission is under the area of Cy5 absorption. Overlapping of all the other acceptor absorbances in FIG. 4 is minor (less than 50% in arbitrary qualitative terms). For comparison, prior art has specified an overlapping integral $J=4.9 \times 10^{12}$ cm$^3$/mol/l to be "very high" (Mathis, Clin Chem 39; 1953, 1993). According to this invention, the overlapping integral J shall be less than this value.

In this invention, the lanthanide chelate used as donor does nor have to show spectral overlapping at least not with the absorptive characteristics of the acceptor. According to the invention, lanthanide chelates behave differently in respect to energy transfer as compared to conventional organic fluorescent compounds. They do not strictly obey the generally accepted rules for resonance energy transfer. The donor acceptor pair can be chosen so that there is little or no spectral overlapping between the emission profile of the donor and absorbance of the acceptor. According to the invention the important factor is not the spectral overlapping (no quantitative relationship between energy transfer and emission spectrum of the donor), but energetic overlapping. Because the inter- and intramolecular energy transfer process is complicated and involves different excited and ground state levels of the ligand and the lanthanide, efficient energy transfer can take place at a wavelength were spectral overlapping is minimal.

Figure 1:
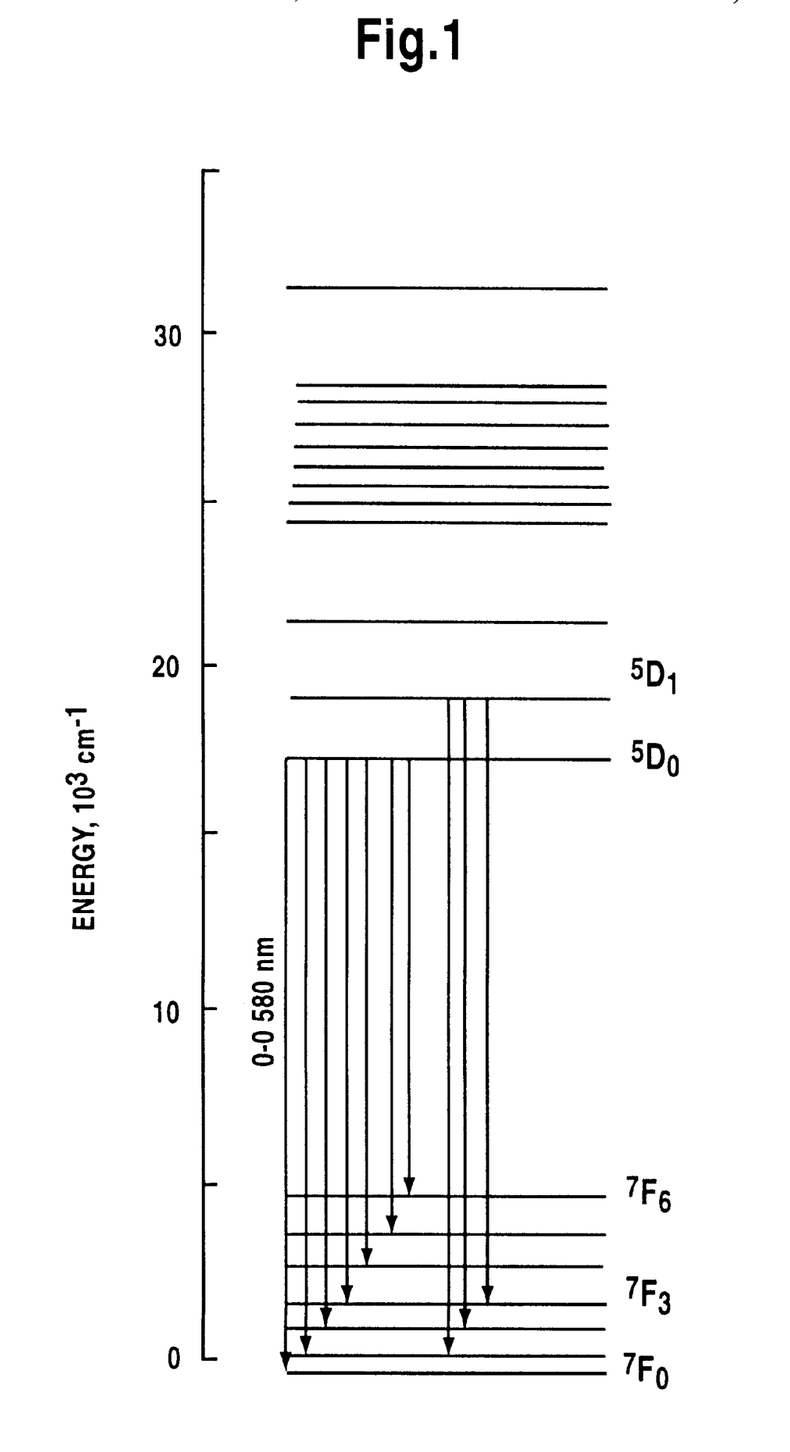
FIG. 1 shows a schematic energy diagram of an $Eu^{3+}$ ion showing some of the excited states and the ground state manifold. Excited state $^5D_1$ takes part in energy transfer from ligand to ion, and $^5D_0$ is the major emittive level. Direct transitions from $^5D_1$ are short-lived and much weaker.

This fact is confirmed with presented examples and has a number of consequences. For the first, assays where dissociation is to be measured, efficient quenching of e.g. Eu chelate can be achieved with a donor (quencher) which has shorter absorption wavelength than the donor's 0—0 transition (FIG. 1 and 4). At short distances an energy transfer takes place from a higher excited state of Eu ($^5D_1$). This level energetically overlaps with the absorption of e.g. rhodamines (at wavelength range of 530–540 nm). For quenching assays, such as helicase in the example, this gives more choice in acceptors, and actually has produced more efficient quenching than a regular spectrally overlapping acceptor (such as Cy5 with Eu).

The second consequence of the nonoverlapping principle is the possibility to lengthen the wavelength range of the donor. The lanthanides have several ground states giving rise to numerous transitions in their emissions. Regardless of the fact that emissions are sharp and well defined, there always tends to be a minor background at the wavelength acceptors are measured. The relative background is, however, less a problem at longer wavelengths. E.g. with Eu there are areas were Eu has a very minor background between 700 and 800 nm and at over 800 nm Eu does not emit any direct emission. With Tb the extended wavelength range gives the possibility to use acceptors emitting at over 700 nm, where Tb does not create any background. By choosing a nonoverlapping wavelength area, the sensitivity and dynamic range of TR-based FRET can be improved.

The third consequence of the invention relates to multiparametric assays. In energy transfer there are two ways to make dual- triple- or multilabel assays. One way is to use different pairs (Eu and Tb with suitable acceptors). The other way according to this invention is to use one generic donor and several, spectrally nonoverlapping acceptors.

The terms "first group" and "second group" shall be understood to include any component such as a bioaffinity recognition component (in reactions where the distance between the groups decreases, e.g. in bioaffinity reactions) or a part of a molecule or substrate (e.g. the distal ends of a peptide molecule the cleavage of which will separate the two labeled groups from each other).

The term "chelate" is defined as a coordination complex where the central ion is coordinated with at least two coordination bonds to a single ligand (multidentate ligand). These may be named by different principles, and names like chelates, supramolecular compounds, complexes, complexones etc. are used, Special types of chelates include macrocyclic complexes, crown ethers, cryptates, calixarenes and so on.

The term "luminescence" shall cover fluorescence, phosphorescence, chemiluminescence, bioluminescence and electro-generated luminescence, photoluminescence, radioluminescence, sonoluminescence, thermoluminescence and triboluminescence.

In assays where association is to be measured and a luminescent, short decay time acceptor and a long decay time lanthanide chelate based donor are used, the emission of acceptor molecules is followed using a delay time i.e. time-resolved fluorometry to avoid the interference of the acceptors direct luminescence (emanating from direct excitation of acceptor). It is desirable to construct the assay in such a way that acceptor molecules are in excess (with time-resolved mode, their interference is negligible) and the energy transfer between donor and acceptor creates an increase in signal.

The sensitivity of any energy transfer based assay depends on both the intensity level of the obtained signal and on the total background. The signal level in a particular assay depends on the used chelate, its total excited state population and duration in the complex. The excited state population is a direct function of luminescent properties of the chelate, i.e. molar absorptivity ($\epsilon$), quantum yield ($\Phi$) and decay time ($\tau$). Accordingly a preferred chelate label has to have high luminescence yield ($\epsilon \times \Phi > 2000$) and long excited state lifetime (preferably over 1 ms). These are features which are particularly expressed in an earlier patent application (WO 98/1 5830).

Good chelates for the present application are Eu chelates formed with multichromogenic polycarboxylates, having high molar absorption coefficient ($\epsilon$), very long excited state lifetime and good quantum yield ($\Phi$) (Takalo et al. Helv Chim Acta 79; 789, 1996). In addition to Eu, Tb is a particularly promising energy donor, when its highly luminescent chelates are used. A preferred Tb chelate is composed of terpyridine derivatives containing the binding site at the iminodiacetate group (Mukkala et al, J Alloys Compounds 225; 507, 1995) or otherwise a binding arm well isolated from the light absorbing aromatic structure.

Particularly good chelates for applications are terpyridine derivatives where one or two pyridine rings are replaced with pyrazole (EP 077061041) or triazole and thiazole rings (WO 93/11433). In addition to Eu and Tb, the use of Sm would give the possibility to make double- or triple-label homogeneous energy transfer assays. Sm has the advantage, that it can donate energy at a rather high wavelength. The major emission of a luminescent Sm chelate is at 643 nm, giving the opportunity to continue with the wavelength scale up to near IR (a good collection of near-IR emitting fluors have become commercially available from different sources). A preferred stable chelate of Sm is composed of multiple forms of 1,3-diketones, such as described by Savitsky (Savitsky et al, SPIE 2388; 429, 1995). An alternative third choice (third label) is the phosphorescent Pt or Pd coproporphyrins emitting a long lifetime phosphorescence at 650–660 nm (WO 94/10568).

A preferred acceptor molecule for association assays is highly luminescent (with quantum yield as near unity (1) as possible) with a high molar absorption coefficient (preferably over 100 000). In all of the prior art known applications a requirement for acceptors relates to the spectral overlapping factor. According to the present invention the absorptivity of the acceptor does not have to overlap with the emission of the donor. However, it is important that the acceptor has a high quantum yield, and emits light at wavelength where the used lanthanide has a minimal background.

The decay-time of the acceptor should be below 1 $\mu$s. In addition the acceptor has to be attached to binding partners, either directly or indirectly (e.g. via anti-binder antibody, lectin, avidin etc.), covalently or noncovalently. As covalently conjugated probes, e.g. those of xanthene dyes (rhodamine, tetramethylrhodamine, Texas Red™ (see e.g. Hemmilä, 1991, Haugland, Handbook of Fluorescent Probes and Research Chemicals, Molecular Probes 1992–1994, Mayer and Neuenhofer, Angew Chem Int Ed Engl 33; 1044. 1994), some carbocyanines (e.g. Cy3.18) (Mujumbar et al, Bioconjugate Chem 4; 1057 1993, Southwick et al, Cytometry 11; 418,1990) and even some porphyrins (Camman, DE 4,216,696)) can be used.

Acceptors for that wavelength range can be found particularly from the group of red light or IR emittive dyes (for reviews see Haugland, Molecular Probes, Miller, Spectroscopy Europe 5; 34, 1993, Patonay and Antoine, Anal Chem 63; 332A, 1991, Southwick et al. Cytometry 11; 418, 1990, Mujumbar et al, Cytometry 10; 11, 1989, Mujumbar et al, Bioconjugate Chem 4; 105, 1993 and Papkovsky, Appl Fluorescence Technol III; 16, 1991, Schindele and Renzoni, J Clin Immunoassay 13; 182,1993). These types of compounds include phthalocyanines, porphyrins, cyanine dyes (Cy5, Cy5.18, Cy5.29) (Selvin et al, J Amer Chem Soc 116; 6029, 1994, Mujumbar et al, Bioconjugate Chem 4; 105, 1993), conjugated xanthenes (rhodamnine 800) (Imasaka et al, Anal Chem 61; 2285, 1989), squarates (Chang, EP 176,252), methylene blue, Nile blue and oxazines (Imasaka et al, Anal Chem 61; 2285, 1989) and indocyanine green (Imasaka et al, Anal Chem 62; 363A, 1990). Some of the phycobiliproteins are good candidates also for Eu acceptors, particularly A-PC, C-PC and R-PC. A preferred energy acceptor for Sm or for coproporphyrins are the IR emittive dyes (see reviews mentioned above).

Preferably, the instrument automatically corrects any attenuation of excitation the sample may cause by simultaneously following the absorbances of the samples diluted into assay mixture and correcting the emission readings according to excitation or emission attenuation by sample absorption.

In homogeneous assays the energy transfer exited acceptor emission may have to be corrected due to various interferences the sample may have, In the correction different parameters, like absorbance measurements, donor and acceptor luminescence intensities and decay times can be used, as described in WO 98/15830.

Preferred chelates for assays based on dissociation are to a great extend the same as described above for association based assays. Terbium, however, is often a better choice, because it can be quenched with a variety of compounds, including metal ions, nitrogen compounds such as azide, nitride (Tanaka et al, J Photochem Photobiol 74; 15, 1993) or radicals (spin labels, such as Doxyl, Proxyl or Tempo and other N—O compounds containing unpaired electrons) (Matko et al, Biochemistry 31; 703, 1992). Good Tb chelates suitable for the present invention are mentioned above. On the other hand Eu can be efficiently quenched by its $^5D_1$ level with spectrally nonoverlapping acceptors, which makes it an interesting acceptor too.

A preferred acceptor for a dissociation measuring assay is a good energy acceptor causing as efficient donor quenching as possible. The acceptor can be luminescent, but does not have to be. A preferred FRET acceptor has good acceptor properties ($R_0$ over 5 nm), but does not have to be highly luminescent. In addition to luminescent compounds mentioned above, a good acceptor can be a respective compound made nonluminescent with heavy atom conjugations (such as erythrosin) or suitable other substituents (see. e.g. Khanna and Ullman, Anal Biochem 108; 156, 1980, Ullman and Khanna, Methods Enzymol 74; 28, 1981). To avoid steric interference (e.g. with HIV peptides labeled both with donor and with acceptor), the acceptor has to be small, and small molecular organic quenchers are preferred. Use of larger acceptors possibly requires indirect approach, i.e. use of a small affinity label (e.g. small hapten, biotin) and a separate step for quenching (e.g. addition of acceptor labeled antihapten of avidin), which may have to be done after the actual dissociation reaction (i.e. end point detection). A preferred assay design for e.g. a peptidase is to use a peptide substrate labeled at one end with a fluorescent terbium or europium chelate and at the other end with a rhodamine derivative.

A preferred acceptor according to present invention is a highly absorbing, small molecular compound. In case of Eu, it may be a compound absorbing at 585–590 nm range (at the 0—0 transition. i.e. the maximum energy level of an excited Eu), it may absorb at higher level (over 600 nm), with substantial or less spectral overlapping features, or surprisingly it may be a compound with absorption maximum below 580 nm. The latter is made possible because the energy transfer, in particular with relatively short distances (1–2 am) is not controlled by the equation presented above (Eq. 1 and 2). One possible explanation is that a higher excited energy level, $^5D_1$ of Eu is involved in intrachelate energy transfer, and that energy is overlapping with the absorption of an eventual acceptor. In practically all highly luminescent Eu chelates the energy mediating ligand has to have its triplet state above the $^5D_1$ level, and the energy flow is through that state (Latva et al. J. Luminescence 75; 149, 1997).

When designed to be quenched in associated form (such as quenched substrate), the donor luminescence and its decay time is increased upon dissociation. So the preferred delay time in measurement is long, to avoid detecting of possible remaining luminescence of the quenched donor. These assays, similar to association assays, are sometimes prone to sample interferences (e.g. color quenching), and the problems can be solved similarly as described above.

EXAMPLES

Example 1

Preparation of Eu-chelate labeled blotin.

A fluorescent Eu-chelate with a free aromatic amino-group was obtained from Wallac labelling service (product W1024). The amino-derivative (81 mg, 0.12 mmol) was dissolved in MES-buffer (0.5M, pH 5.5, 1.5 ml) and a solution of biotin (25 mg, 0.1 mmol)) was added followed by 20 mg of EDAC (0.1 mmol). The mixture was stirred for 4.5 h at room temperature. The solution was concentrated to 1 ml and the labeled biotin precipitated with acetone.. The product was purified with TLC and with gel filtration.

Example 2

Preparation of Tb-chelate labeled biotin.

A long spacer and biotin was prepared as follows. A solution of BOC-ON (4,93 mg, 20 mmol) and TEA (4.2 ml) in 1,4-dioxane (20 ml) was slowly added into a solution of 1,6-diaminohexane (4.65 mg, 40 mmol) in 1,4-dioxane (18 ml). After 22 h continuous mixing at room temperature the mixture was filtered and the filtrate evaporated to dryness. The residue was suspended in water and the insoluble material was filtrated. The filtrate was extracted with $CH_2Cl_2$ and organic phase was dried with sodium sulphate. The product was purified by flash chromatography on silica gel. Yield 61%.

The compound prepared above (0.11 g, 0.5 mmol) was dissolved in dry DMF (6 ml) and dry pyridine (2 ml). Dry TEA (0.5 ml) and biotin-NHS (0.17 g, 0.5 mmol) was added. The mixture was stirred for 20 h at room temperature and evaporated to dryness. The product was precipitated from $CH_2Cl_2$. The protective group was hydrolyzed by treating the compound (26 mg, 59 $\mu$mol) in 6 ml of $CHCl_3$ with a dry $HCl/CH_3OH$ mixture (1 ml) for 3 h at room temperature. The product was evaporated to dryness and purified on preparative TLC.

Coupling of the biotin derivative to a Tb-chelate: The biotin derivative prepared above was dissolved into a mixture of pyridine/$H_2O$/TEA (9/1.5/0.1 in volume ratios). An isothiocyanate activated fluorescent Tb chelate, obtained from Wallac (product W14016), was let to react with the aminogroup on the biotin derivative in aqueous solution. After overnight incubation at room temperature the conjugate was concentrated under reduced pressure and purified on preparative TLC and gel filtration.

Example 3

Measurement of energy transfer between Eu chelate labeled biotin and acceptor molecules attached with streptavidin.

The following labeled streptavidins were used as such. Streptavidin labeled with FITC, Rhodamine B, TRITC, Rhodamine Red. Alexa 488, Alexa 532, Alexa 546 and Malachite Green were purchased from Molecular Probes (Eugene, Oreg.). Cryptofluors™, CF-1, CF-2, CF-3 and CF-4, labeled streptavidins were from Intergen (Purchase, N.Y.). Cy5 were obtained from Amersham-Pharmacia and IR emitting probes IRD-40 and NN 389 from Li-Cor (Lincoln, Nebr.). All were conjugated with streptavidin with standard methods with an average yield of 2–5 dyes per streptavidin.

In an assay buffer (Tris-buffered saline, pH 7.7 containing 0.5% bovine serum albumin) 10 nM of Eu-labeled biotin were incubated with 4 nM of labeled streptavidin for 30 min and Eu fluorescence was read with a time resolved fluorometer (1420 Victor, Wallac) using factory made Eu measuring protocol. The energy transfer was calculated from Eu quenching with the following results:

TABLE 1

| Acceptor | Absorbance nm | Quenching of Eu (613 nm) |
| --- | --- | --- |
| FITC | 495 | 80% |
| Eosin | 524 | 65% |
| Rhodamine B | 570 | 94% |
| TRITC | 543 | 99% |
| Rhodamine Red | 570 | 95% |
| Texas Red | 595 | 96% |
| Alexa 488 | 495 | 58% |
| Alexa 532 | 530 | 91% |
| Alexa 546 | 555 | 61% |
| Cy5 | 610, 650 | 97% |
| Malachite Green | 630 | 71% |
| Cryptofluor 1 (CF-1) | 575, 612 | 77% |
| CF-2 | 585, 645 | 76% |
| CF-3 | 545, 560 | 54% |
| CF-4 | 555 | 58% |
| IRD 40 | 768 | 91% |
| NN386 | 786 | 96% |

In the model binding assay Eu was quenched by resonance energy transfer both with acceptors having their absorbances below 0—0 transition (<580 nm), with acceptors with overlapping absorbance (Cy5) and with acceptors with little or almost TAO overlapping at longer wavelengths.

Example 4

Quenching of Tb-labeled biotin with acceptor-labeled streptavidin

The quenching of terbium-labeled biotin was studied in a similar test as used in Example 2. Efficient energy transfer is recorded regardless of the spectral overlapping factor.

TABLE 2

| Acceptor | Absorbance, nm | Quenching of Tb (545 nm) |
| --- | --- | --- |
| FITC | 494 | 99% |
| Eosin | 524 | 97% |
| TRITC | 543 | 99% |
| Rhodamine Red | 570 | 99% |
| Texas Red | 595 | 99% |
| Alexa 488 | 495 | 99% |
| Alexa 532 | 530 | 99% |
| Alexa 546 | 555 | 98% |
| Cy5 | 610, 650 | 99% |
| Malachite Green | 630 | 87% |
| Cryptofluor 1 (CF-1) | 575, 612 | 95% |
| CF-2 | 585, 645 | 89% |
| CF-3 | 545, 560 | 92% |
| CF-4 | 555 | 88% |

Similarly to Example 3 with Eu, Tb was quenched by resonance energy transfer by various compounds and no correlation was found between energy transfer and spectral overlapping.

Example 5

Labeling of anti-β-hCG (human chorionic gonadotropin) antibody (code F19-9C1) with a fluorescent terbium chelate.

The emission maximum of the terbium (Tb) chelate W14016 (Wallac Oy, Turku, Finland) is at 545 nm. The Tb chelate was conjugated to anti-β-hCG antibody (code F19-9C1, Wallac Oy) in the following way: anti-β-hCG antibody (5 mg/ml) was incubated with a 60-fold molar excess of the Tb chelate in 50 mM carbonate buffer pH 9.5 over night at +4° C. The labeled antibodies were separated from free Tb chelate by gel filtration (Sepharose 6B with Sephadex 050 overlay, 0.5×70 cm, Pharmacia, Uppsala, Sweden) with Tris (50 mM Tris-HCl, pH 8 containing 0.9% NaCl) as elution buffer. The labeled antibody was analyzed and found to contain 8.7 Tb per antibody. Labeled antibody was kept in Tris buffer, pH 7.4 containing 0.1% bovine serum albumin.

Example 6

Labeling of anti-β-hCG (code M15294) antibody with the fluorescent cyanine dye Cy3

The absorption maximum of the cyanine dye Cy3 (Amersham Life Science) is at 550 nm and emission maximum is at 570 nm. Cy3 (acceptor) was conjugated to anti-β-hCG antibody (code M15294, Wallac Oy) in the following way: anti-β-hCG antibody (5 mg/ml) was incubated with a 30-fold molar excess of Cy3 in 50 nM carbonate buffer pH 9.3. After 30 min. of incubation at room temperature the labeled antibodies were separated from unreacted Cy3 by gel filtration (Sepharose 6B with Sephadex G50 overlay, 0.5×70 cm, Pharmacia) with Tris (50 mM Tris-HCl, pH 7.7 containing 0.9% NaCl) as elution buffer. The labeled antibody was analyzed and found to contain 1.8 Cy3 per antibody. Labeled antibody was kept in Tris buffer, pH 7.4 containing 0.1% bovine serum albumin.

Example 7

Labeling of anti-β-hCG (code M15294) antibody with the fluorescent cyanine dye Cy5

The absorption maximum of the cyarine dye Cy5 (Amersham Life Science) is at 649 nm and emission maximum is at 670 nm. Cy5 (acceptor) was conjugated to anti-β-hCG antibody (code M15294, Wallac Oy) in the following way: anti-β-hCG antibody (5 mg/ml) was incubated with a 30-fold molar excess of Cy5 in 50 mM carbonate buffer pH 9.3. After 30 min of incubation at room temperature the labeled antibodies were separated from unreacted Cy5 by gel filtration (Sepharose 6B with Sephadex G50 overlay, 0.5×70 cm, Pharmacia) with Tris (50 mM Tris-HCl, pH 7.7 containing 0.9% NaCl) as elution buffer. The labeled antibody was analyzed and found to contain 2.4 Cy5 per antibody. Labeled antibody was kept in Tris buffer, pH 7.4 containing 0.1% bovine serum albumin.

Example 8

Homogenous energy transfer assay of β-hCG with Cy3 or Cy5 as acceptors.

In this two-site immunoassay, 50 μl of β-hCG standard in the wells of 96-well plates were incubated with 100 ng of Tb labeled antibody (donor) and 100 ng of Cy3 or Cy5 labeled antibody (acceptor) in 200 μl Tris buffer, pH 7.4. The two anti-β-hCG antibodies used are directed against different specific antigenic sites on the β-hCG subunit. The β-hCG standards were from a commercially available kit for the measurement of free hCGβ in serum (Wallac Oy). The reaction mixtures were incubated for 60 min at room temperature. The fluorescence from energy transfer excited Cy3 or Cy5 in the formed complexes was measured in a time-resolved fluorometer, model 1420 Victor (Wallac Oy). Fluorometer settings for the measurement of Cy3 were excitation at 340 nm, emission at 570 nm, delay time 50 μs, window time 100 μs, cycling time 1 ms and for Cy5 excitation at 340 nm, emission at 665 nm, delay time 50 μs, window time 100 μs, cycling time 1 ms. A set of β-hCG standards analyzed with the homogeneous assay for β-hCG were obtained:

TABLE 3

| | Fluorescence (cps) | |
|---|---|---|
| β-hCG ng/ml) | Cy3 | Cy5 |
| 0 | 1827 | 1697 |
| 2 | 2069 | 1912 |
| 5 | 2413 | 2191 |
| 19 | 3587 | 3465 |
| 98 | 7854 | 8238 |
| 198 | 9769 | 11880 |

Regardless of the fact that Cy3 (excitation at 552 and emission at 565 nm) is the spectrally overlapping pair for Tb, Cy5 (excitation at 610–650 nm) gave better sensitivity in the assay. This demonstrates the unimportance of spectral overlapping in choosing acceptors.

Example 9

Synthesis of complementary oligonucleotides using phosphoramidite chemistry

The following oligonucleotides complementary to each other were synthesized using phosphoramidite chemistry using a DNA/RNA Synthesizer of Applied Biosystem Model 392:

OL1 5'-AXg CgT Tgg AAC CTg gAT AgC TTA
    ggC CTA-3'                                    (SEQ ID NO:1)

OL2 5'-TAg gCC TAA gCT ATC CAg gTT CCA
    ACg XgT-3'                                    (SEQ ID NO:2)

where X denotes a deoxycytidine residue having 6-aminohexyl linker arm attached to exocyclic amino group at 4 position in the base moiety. Oligonucleotides were purified using polyacrylamide gel electrophoresis.

Example 10

Labeling of OL1 with a fluorescent europium chelate

Oligonucieotide OL1 (200 μg, 20.2 nmol) was evaporated to dryness and dissolved in 50 μl water. Dichlorotriazine-activated fluorescent europium (Eu) chelate (W8044, Wallac) was dissolved in 100 μl water and chelate concentration was determined by making a total dilution of 1:50 000 000 in DELFIA Enhancement solution and measuring against 1 nM europium standard in a VICTOR Multilabel counter (Wallac) using time-resolved fluorometry mode. Eu chelate (15 mM, 54 μl, 810 nmol) was added to the oligonucieotide solution followed by 12 μl 1M sodium carbonate pH 9.5 The reaction was allowed to proceed at room temperature for 18 hours.

Eu-labeled oligonucleotide OL1 was purified from the unreacted chelate and unlabeled oligonucleotide using reverse phase HPLC and acetonitrile gradient in 0.1M triethylammonium acetate pH 7. After collecting Eu-labeled OL1 acetonitrile was removed by vacuum centrifugation. Subsequently Eu-labeled oligonucleotide was run through a short Sephadex G-25 (NAP-5, Pharmacia) column using 20 mM Tris-HCl pH 8 containing 50 mM NaCl.

The labeled OL1 was characterized by measuring Eu concentration against Eu standard and by running an absorbance spectrum from 200 nm to 400 nm. The labeled oligonucleotide contained one europium chelate per each oligonucleotide molecule.

Example 11

Labeling of OL2 with tetramethylrhodamine

Oligonucleotide OL2 (200 μg, 20.2 nmol) was evaporated to dryness and then dissolved in 125 μl water. Tetramethylrhodamine isothiocyanate (TRITC) (Molecular Probes) was dissolved in dry dimethylformamide to a concentration of 25 mM. TRITC (25 μml, 625 nmol) was added to the oligonucleotide solution. To adjust pH of the reaction mixture 17 μl 1M sodium carbonate pH 9.5 was added, The reaction mixture was incubated protected from light at RT 19 hours.

TRITC-labeled oligonucleotide OL2 was purified using reverse phase HPLC and acetonitrile gradient in 0.1M triethylammonium acetate pH 7. After evaporating acetonitrile TRITC-labeled OL2 was further purified using a short Sephadex G-25 column as above for Eu-labeled OL1.

TRITC-labeled oligonucleotide OL2 was characterized by running an absorption spectrum from 200 nm to 650 nm. Characterization gave a labeling degree of one TRITC per oligonucleotide.

Example 11

Efficiency of quenching

To study the efficiency of TPITC to quench Eu fluorescence 50 nM Eu-labeled OL1 was annealed with 150 nM TRITC-labeled OL2. For comparison 50 nM Eu-labeled OL1 was hybridized with 150 nM unlabeled OL2. Annealing solution contained 0.4M NaCl in 20 mM Tris-HCl pH 8 and reactions were incubated at 35° C. for 4 hours. After annealing samples (200 μl) of both reactions were pipetted into clear 96-well miicrotitation plate. The wells were measured in a VICTOR Multilabel counter using factory set parameters for Eu measurement. Eu-labeled OL1 annealed with unlabelled OL2 gave 4 238 000 cps whereas Eu-labeled OL1 hybridized with TRITC-labeled OL2 gave 318 000 cps. These results indicate that when Eu chelate in OL1 was in close proximity with TRITC in OL2, then 92.5% of Eu fluorescence was quenched.

We claim:

1. A luminescence energy transfer based bioaffinity assay comprising a first group labeled with an energy donating compound (donor) and a second group labeled with an energy accepting compound (acceptor), wherein the donor is a luminescent lanthanide chelate having a long excited state lifetime and the acceptor is either a luminescent compound having a short excited state lifetime or a nonluminescent compound, and the increase or decrease, respectively, in the energy transfer from the donor to the acceptor resulting from shortening or lengthening, respectively, of the distance between the said groups, is measured characterized in that the lanthanide energy emission and the acceptor energy absorption do not essentially or not at all overlap each other.

2. The assay according to claim 1, characterized in that the acceptor is chosen so that its emission takes place at a wavelength range where the donor does not emit.

3. The assay according to claim 1, characterized in that the acceptor energy absorption takes place at a wavelength range where the wavelength is longer than that of the lanthanide emission.

4. The assay according to claim 3, characterized in that the donor is a chelate of europium and that the wavelength of the acceptor emission is over 700 nm.

5. The assay according to claim 3, characterized in that the acceptor is selected from a group consisting of long wavelength emitting cyanines, squarates, porphyrins and oxazines.

6. The assay according to claim 3, characterized in that the increase in energy transfer from the donor label to the acceptor label resulting from shortening of the distance between said labels, is measured.

7. The assay according to claim 3, characterized in that two or more analytes are simultaneously measured, wherein     each analyte is measured by a specific donor-acceptor pair, where the donors comprise the same or different lanthanides, and where     at least one of the acceptors is an agent having energy absorption and energy emission at a wavelength range in which the wavelength is longer than in the region for the energy emission of the lanthanide in the same donor-acceptor pair.

8. The assay according to claim 1, characterized in that the acceptor energy absorption takes place at a wavelength range were the wavelength is shorter than that of lanthanide energy emission.

9. The assay according to claim 8, characterized in that the lanthanide is europium or terbium and that the acceptor is a light absorbing compound.

10. The assay according to claim 8, characterized in that the decrease in energy transfer resulting from lengthening of the distance between said labels is measured.

11. The assay according to claim 8, characterized in that the increase in donor emission resulting from lengthening of the distance between said labels is measured.

12. The assay according to claim 10, characterized in that one strand of a double-stranded nucleic acid is labeled with the donor and the other strand is labeled with the acceptor, and that the dissociating effect of an enzyme on the double-stranded nucleic acid is measured.

13. The assay according to claim 11, characterized in that one strand of a double-stranded nucleic acid is labeled with the donor and the other strand is labeled with the acceptor, and that the dissociating effect of an enzyme on the double-stranded nucleic acid is measured.

\* \* \* \* \*

```
                      SEQUENCE LISTING

<160> NUMBER OF SEQ ID NOS: 2

<210> SEQ ID NO 1
<211> LENGTH: 30
<212> TYPE: DNA
<213> ORGANISM: synthesized DNA oligo
<220> FEATURE:
<221> NAME/KEY: modified_base
<222> LOCATION: (2)
<223> OTHER INFORMATION: "n" at location 2 is a deoxycytidine residue
      having a 6-aminohexyl linker arm attached to an exocyclic amino
      group at 4 position in the base moiety.

<400> SEQUENCE: 1
angcgttgga acctggatag cttaggccta                                    30

<210> SEQ ID NO 2
<211> LENGTH: 30
<212> TYPE: DNA
<213> ORGANISM: synthesized DNA oligo
<220> FEATURE:
<221> NAME/KEY: modified_base
<222> LOCATION: (28)
<223> OTHER INFORMATION: "n" at location 28 is a deoxycytidine residue
      having a 6-aminohexyl linker arm attached to an exocyclic amino
      group at 4 position in the base moiety.

<400> SEQUENCE: 2
taggcctaag ctatccaggt tccaacgngt                                    30
```